United States Patent
Auberger et al.

(10) Patent No.: US 11,931,273 B2
(45) Date of Patent: *Mar. 19, 2024

(54) METHOD FOR CONTROLLING AN ARTIFICIAL ORTHOTIC OR PROSTHETIC KNEE JOINT

(71) Applicant: OTTO BOCK HEALTHCARE PRODUCTS GMBH, Vienna (AT)

(72) Inventors: Roland Auberger, Vienna (AT); Martin Seyr, Vienna (AT); Clemens Mandl, Vienna (AT); Dirk Seifert, Perchtoldsdorf (AT); Hans Dietl, Gablitz (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 251 days.

This patent is subject to a terminal disclaimer.

(21) Appl. No.: 17/201,955

(22) Filed: Mar. 15, 2021

(65) Prior Publication Data

US 2021/0369474 A1  Dec. 2, 2021

Related U.S. Application Data

(63) Continuation of application No. 15/920,176, filed on Mar. 13, 2018, now Pat. No. 10,945,863, which is a
(Continued)

(30) Foreign Application Priority Data

Aug. 22, 2013 (DE) .......................... 102013013810.8

(51) Int. Cl.
*A61F 2/64* (2006.01)
*A61F 2/68* (2006.01)
(Continued)

(52) U.S. Cl.
CPC .................. *A61F 2/70* (2013.01); *A61F 2/64* (2013.01); *A61F 2/68* (2013.01); *A61F 5/0123* (2013.01);
(Continued)

(58) Field of Classification Search
None
See application file for complete search history.

(56) References Cited

U.S. PATENT DOCUMENTS

| 6,423,098 B1 | 7/2002 | Biedermann |
| 6,755,870 B1 | 6/2004 | Biedermann et al. |

(Continued)

FOREIGN PATENT DOCUMENTS

| CN | 101128167 A | 2/2008 |
| CN | 101437470 A | 5/2009 |

(Continued)

OTHER PUBLICATIONS

PCT International Search Report for PCT International Patent Application No. PCT/EP2014/001869, dated Oct. 10, 2014.
(Continued)

*Primary Examiner* — David H Willse
(74) *Attorney, Agent, or Firm* — HOLLAND & HART LLP

(57) ABSTRACT

A method for controlling an artificial orthotic or prosthetic knee joint, on which a lower-leg component is arranged and with which a resistance device is associated, the bending resistance (R) of which resistance device is changed in dependence on sensor data that are determined by at least one sensor during the use of the orthotic or prosthetic knee joint, wherein a linear acceleration ($a_F$) of the lower-leg component is determined, the determined linear acceleration ($a_F$) is compared with at least one threshold value, and, if a threshold value of the linear acceleration ($a_F$) of the lower-
(Continued)

leg component is reached, the bending resistance (R) is changed.

19 Claims, 3 Drawing Sheets

Related U.S. Application Data continuation of application No. 14/911,549, filed as application No. PCT/EP2014/001869 on Jul. 7, 2014, now Pat. No. 9,968,468.

(51) Int. Cl.
*A61F 2/70* (2006.01)
*A61F 5/01* (2006.01)
*A61F 2/48* (2006.01)
*A61F 2/50* (2006.01)
*A61F 2/76* (2006.01)

(52) U.S. Cl.
CPC ....... *A61F 2/482* (2021.08); *A61F 2002/5007* (2013.01); *A61F 2002/503* (2013.01); *A61F 2002/5033* (2013.01); *A61F 2002/5072* (2013.01); *A61F 2002/6818* (2013.01); *A61F 2002/704* (2013.01); *A61F 2002/7625* (2013.01); *A61F 2002/764* (2013.01); *A61F 2002/7645* (2013.01); *A61F 2005/0155* (2013.01); *A61F 2250/0012* (2013.01); *A61F 2250/0096* (2013.01)

(56) References Cited

U.S. PATENT DOCUMENTS

| | | | |
|---|---|---|---|
| 7,731,759 B2 | 6/2010 | Pusch et al. | |
| 9,968,468 B2* | 5/2018 | Auberger | A61F 5/0123 |
| 10,945,863 B2* | 3/2021 | Auberger | A61F 5/0123 |
| 2006/0135883 A1 | 6/2006 | Jonsson et al. | |
| 2006/0224247 A1 | 10/2006 | Clausen et al. | |
| 2007/0010772 A1 | 1/2007 | Ryan | |
| 2009/0076618 A1 | 3/2009 | Auberger | |
| 2009/0192619 A1 | 7/2009 | Martin et al. | |
| 2010/0228360 A1 | 9/2010 | Pusch et al. | |
| 2010/0305716 A1* | 12/2010 | Pusch | A61F 2/68 623/24 |
| 2012/0221120 A1 | 8/2012 | Seyr et al. | |
| 2012/0226364 A1 | 9/2012 | Kampas et al. | |
| 2012/0232674 A1* | 9/2012 | Kampas | A61F 2/64 623/24 |
| 2014/0379096 A1 | 12/2014 | Zahedi et al. | |
| 2015/0001897 A1 | 1/2015 | Tsai | |
| 2015/0018972 A1 | 1/2015 | Albrecht-Laatsch | |

FOREIGN PATENT DOCUMENTS

| | | |
|---|---|---|
| CN | 101453963 A | 6/2009 |
| DE | 19859931 A1 | 7/2000 |
| DE | 102008027639 A1 | 12/2009 |
| DE | 102009052887 A1 | 5/2011 |
| DE | 102009052894 A1 | 6/2011 |
| DE | 102012003369 A1 | 8/2013 |
| EP | 1237513 B1 | 10/2004 |
| IN | 102762171 A | 10/2012 |
| JP | 01-244748 A | 9/1989 |
| JP | 2001-511052 A | 8/2001 |
| JP | 2011-502593 A | 1/2011 |
| JP | 2013-510605 A | 3/2013 |
| JP | 2013-212260 A | 10/2013 |
| JP | 2015-505701 A | 2/2015 |
| RU | 2032434 C1 | 4/1995 |
| RU | 2089138 C1 | 9/1997 |
| RU | 2121823 C1 | 11/1998 |
| RU | 2484789 C2 | 6/2013 |
| WO | 2007/128299 A1 | 11/2007 |
| WO | 2009/059594 A2 | 5/2009 |
| WO | 2011/057795 A1 | 5/2011 |
| WO | 2012/100250 A1 | 7/2012 |
| WO | 2013/088142 A1 | 6/2013 |

OTHER PUBLICATIONS

Wikipedia—Inertial Measurement Unit, downloaded on Jun. 17, 2020.

* cited by examiner

METHOD FOR CONTROLLING AN ARTIFICIAL ORTHOTIC OR PROSTHETIC KNEE JOINT

CROSS-REFERENCE TO RELATED APPLICATIONS

This is a continuation application of U.S. patent application Ser. No. 15/920,176, filed 13 Mar. 2018, and entitled METHOD FOR CONTROLLING AN ARTIFICIAL ORTHOTIC OR PROSTHETIC KNEE JOINT, issued as U.S. Pat. No. 10,945,863 on 16 Mar. 2021, which is a continuation application of U.S. patent application Ser. No. 14/911,549, filed 11 Feb. 2016, and entitled METHOD FOR CONTROLLING AN ARTIFICIAL ORTHOTIC OR PROSTHETIC KNEEJOINT, issued as U.S. Pat. No. 9,968,468 on 15 May 2018, which is a U.S. National Entry Application from International Patent Application No. PCT/EP2014/001869, filed 7 Jul. 2014, and also entitled METHOD FOR CONTROLLING AN ARTIFICIAL ORTHOTIC OR PROSTHETIC KNEE JOINT, which claims the benefit of German Patent Application No. 102013013810.8, filed 22 Aug. 2013, the disclosures of which are incorporated, in their entireties, by this reference.

TECHNICAL FIELD

The invention relates to a method for controlling an artificial orthotic or prosthetic knee joint, on which a below-knee component is arranged and which is assigned a resistance de ice in which the flexion resistance is changed in accordance with sensor data that are determined via at least one sensor during the use of the orthotic or prosthetic knee joint.

BACKGROUND

Prosthetic or orthotic knee joints replace or support the function of a natural knee joint. In order to achieve a maximally optimal functionality of the artificial knee joint, there are many designs on the market which influence the behavior of the knee joints during the stance phase and the swing phase. Mechatronic knee joints are known, in which the movement situations are detected via a plurality of different sensors and the sensor data are used to control a resistance device via which the flexion resistance or the extension resistance is varied. One basic problem is that the great variety of the possible movement situations can be encompassed only with difficulty in simple rules. Therefore, in order to control actuators and brakes, so-called state machines are used, which are highly complex and represent many different activities. Disadvantages with this are the long development time and the use of elaborate components.

EP 1 237 513 B1 relates to a supporting device which replaces the existence or function of a limb and which consists of at least two parts, connected to each other by an artificial joint, and a control device. The supporting device comprises a sensor, which detects an inclination angle relative to a line of gravity of a part connected to the joint and is coupled to the control device. The control device is arranged in such a way that it influences the joint on the basis of inclination angle data communicated by the sensor. In one configuration, the inclination angle sensor is arranged as a prosthetic knee joint on a thigh tube; in order to enhance the data situation, a second sensor can be arranged on the lower leg.

DE 10 2008 027 639 A1 relates to an orthotic joint for supporting an anatomical knee joint, having an upper joint part and a lower joint part which are connected to each other in an articulated manner. A locking element for automatically unlocking and locking the orthotic joint in an arbitrary position is provided, likewise an actuation element for the locking element and a sensor means for detecting relevant information for the unlocking and locking. An evaluation unit for evaluating the information acquired, and for forwarding this information to a control and/or regulating unit for the actuation element, is likewise present. The sensor means comprises at least two sensors from the group including inclination sensors, rotation angle sensors, acceleration sensors or gyroscopes, for acquiring information describing the movement state and/or resting state of a person. Two sensors of one type or one sensor each of different types may be selected. All the sensors are arranged downward from the anatomical joint, in particular knee joint.

SUMMARY

The object of the present invention is to make available a method for controlling an artificial orthotic or prosthetic knee joint, with which method a reliable gait pattern can be achieved with minimal outlay in control terms.

According to the invention, this object is achieved by a method having the features of the main claim.

Advantageous embodiments and refinements of the invention are disclosed in the dependent claims, the description and the figures.

In the method for controlling an artificial orthotic or prosthetic knee joint on which a below-knee component is arranged and which is assigned a resistance device in which the flexion resistance is modified in accordance with sensor data that are determined via at least one sensor during the use of the orthotic or prosthetic knee joint, provision is made that a linear acceleration of the below-knee component is determined, and, if a limit value of a linear acceleration of the below-knee component is not reached, the flexion resistance is changed, in particular reduced. With the proposed method, it is possible for a knee joint, by which are understood both orthotic knee joints and also prosthetic knee joints, to be controlled exclusively by simple sensors, without elaborate and delicate force measurements having to be carried out. In particular, the use of DMS applications is thereby made redundant.

In a development of the invention, provision is made that an extended stride position of a prosthesis or orthosis with a prosthetic or orthotic knee joint is determined and, when the extended stride position is present, the flexion resistance is reduced. The extended stride position is present when the knee angle is 0° or the knee joint is minimally bent, i.e. has a flexion angle within a range of ±5°. If the extended stride position is present, it can be assumed that the user of the knee joint is in the terminal stance phase, and therefore a reduction in resistance can take place.

In order to detect a terminal stance phase, an absolute angle of the below-knee component can additionally be determined, and, if a predefined limit value for the absolute angle of the below-knee component is exceeded, the flexion resistance can be reduced. From the inclination angle of the below-knee component with respect to the vertical, meaningful conclusions can be drawn concerning the particular phase within a stride, such that the absolute angle is a good indicator of the change, in particular the reduction, of the flexion resistance.

The absolute angle of the below-knee component can be determined from an absolute angle of a thigh component and from a known, e.g. measured, knee angle or can be measured directly with an inertial angle sensor, which is secured on the below-knee component.

Moreover, provision can be made that the knee angle is additionally determined via a knee angle sensor, and, if a limit value for the knee angle is not reached, the flexion resistance is reduced, since the knee angle is an indicator of the state of extension of the leg or of the prosthesis and, consequently, of the particular phase within a step cycle. The knee angle can also be determined from the inertial angles of the thigh and of the lower leg.

If several parameters are available, for example the exceeding of a limit value for the absolute angle of the below-knee component, the falling below a limit value for the knee angle and the falling below a limit value of an acceleration of the below-knee component, it can be more safely assumed that the flexion resistance is intended to be changed, in particular reduced, in order to allow a swing phase to be enabled. With the proposed method, it is possible to safely control a knee joint exclusively via simple sensors.

The majority of microprocessor-controlled prosthetic and orthotic systems are controlled by measurements of force and moment being carried out by means of strain gauges, the decisive aspect for the safety of a knee joint being the change from a high flexion resistance in the stance phase to a low flexion resistance during the swing phase and vice versa. The change-over is also referred to as enablement of the swing phase. In addition to the calculation of bending moments at the ankle level or of the knee moment, threshold values of the values calculated from the strain gauges have to be exceeded in order to enable the swing phase. Furthermore, the enablement of the swing phase often takes place only after a certain forward inclination, such that walking with small steps becomes difficult.

In the method according to the invention, the knee joint is controlled exclusively by knee angle sensors and inertial sensors from whose data the necessary parameters or auxiliary values can be calculated. The absolute angle of the below-knee component, i.e. the inclination of the longitudinal extent of the below-knee component with respect to the vertical, is determined via the inertial sensor. The absolute angle must exceed a minimum value in order to detect a forward inclination of the below-knee component, i.e. an inclination in the walking forward direction. Only at a certain angle in forward inclination can it be assumed that a step in the forward direction is to be taken. The knee angle is determined via a knee angle sensor. If a limit value for a knee angle is not reached, this is a sign that the user is in a terminal stance phase, such that an enablement of the swing phase and therefore a reduction of the flexion resistance are indicated. In addition, the acceleration of the below-knee component is determined. If an acceleration limit value is not reached, it can be assumed that the foot component, for example the foot plate or the prosthetic foot, is still located on the ground, and it is therefore ascertained that the patient is in the terminal stance phase of a stride and the flexion resistance can thus be reduced.

In a development of the invention, provision is made that the knee angle velocity is determined, and the flexion resistance is reduced only when a value for the knee angle velocity is exceeded. A minimum knee angle velocity should be present, since otherwise a stance situation may arise in which a reduction of the flexion resistance may be undesired. With the low or relatively low knee angle velocity, it is additionally ensured that the patient is in the terminal stance phase during a forward movement.

An angular velocity of the below-knee component can be calculated or can be detected via a sensor, for example from the sensor data of a gyroscope. The calculated or detected value of the angular velocity is compared with a limit value, and the flexion resistance is reduced only when the angular velocity is below a limit value.

The linear acceleration of the below-knee component is advantageously determined or measured at the sole level and is used as a basis for the control; the acceleration at the sole level derives from the linear accelerations at the position of the acceleration sensor, for example below the knee joint axis, the angular acceleration of the below-knee component as a first-order derivative of a gyroscope signal, and the location vector of the position of the acceleration sensor to the reference position on the foot, for example on the forefoot. From the linear accelerations at the sole level, conclusions are drawn concerning the kinematic contact condition between the foot or foot part and the ground or concerning the dynamics of the movement, and it is possible to determine in which phase of a stride the patient is located. If there is no linear acceleration or only a very slight linear acceleration, the foot, by which is also understood a prosthetic foot or a foot part of an orthosis, is still located in the stance phase, of if there is also no longer any vertical acceleration, the set-down phase is ended, such that the linear accelerations can be used to draw conclusions regarding the orientation and positioning of the leg. For example, the accelerations can be used to determine corresponding speeds, which can likewise be suitably used for the control.

In a development of the invention, provision is made that the reduction of the flexion resistance takes place when there is a hyperextension of the below-knee component, i.e. that the hyperextension is one of those parameters that are used as controls to change the flexion resistance. The knee angle of 0° is assumed if the below-knee component bears without force on an extension stop. An increase in the knee angle is assumed if a bending of the knee Mint is performed counter to the walking direction. If the knee is hyperextended, the knee angle decreases further, since it is regarded as a negative knee angle. If the knee joint experiences an extension moment about the knee axis as a result of forces acting on the joint, for example via the around reaction force, stump forces or hip moments, a hyperextension may occur which, when detected, can signal that the patient is in the terminal stance phase and, therefore, a swing phase should be enabled.

The knee joint can have an elastic extension stop, for example in order to prevent the below-knee component from swinging hard against the stop in an extension movement. The elastic extension stop can be composed of elastomer bodies, spring elements or the like. By virtue of the elastic extension stop, it is possible to permit a hyperextension in a small angle range when an extension moment is applied about the knee axis, and, when the extension moment ceases, the below-knee component is brought back by the elastic extension stop to the extended or almost extended position, in which the knee angle is 0°. After the load has been removed, the joint returns to the extended or almost extended position. Knowing the spring characteristics of the extension stop and the negative knee angle, it is possible to calculate a knee moment acting in the extension direction about the knee joint and, when a knee moment is present in the extension direction, i.e. when the elastic extension stop is compressed, to reduce the flexion resistance. The knee moment is calculated on the basis of the knee angle and on the knowledge of the spring characteristic, and force measurement sensors or moment sensors are not needed. If there is a knee moment in the extension direction, this is a further factor for ascertaining in which phase of a step the patient is located and whether a swing phase takes place directly and, accordingly, the flexion resistance should be reduced.

A rotation direction of the below-knee component can be calculated or detected via a sensor, for example a gyroscope. The flexion resistance is reduced only if there is a forward rotation of the below-knee component, in order to rule out the possibility of the flexion resistance being undesirably reduced when walking backward.

Acceleration data of the below-knee component can be determined via an acceleration sensor in order to be able to derive or calculate required parameters.

After a reduction of the flexion resistance, the latter can be increased again, in particular to a stance phase level or to such a high level that unwanted bending is not possible or is possible only slowly, if, within a predefined time interval, no bending of the knee joint takes place, or if, within a flexion angle after bending, a previously established limit value for a horizontal acceleration is exceeded. This serves to increase the stability if a swing phase is discontinued, i.e. if no complete step cycle can be performed.

BRIEF DESCRIPTION OF THE DRAWINGS

An illustrative embodiment of the invention is explained in more detail below with reference to the figures, in which.

DETAILED DESCRIPTION

Figure 1:
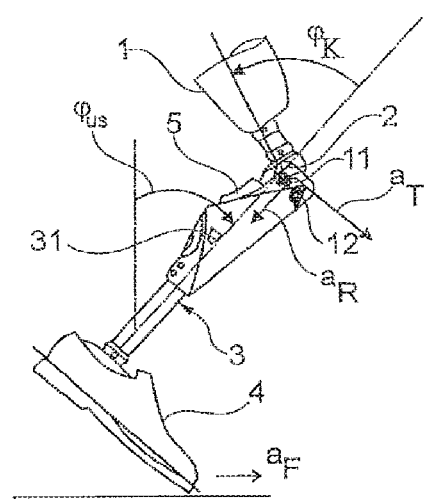
FIG. 1 shows a schematic representation of a prosthetic knee joint.

FIG. 1 shows a prosthetic device for patients with a thigh stump and with no knee joint and lower leg. A prosthesis socket 1, also designated as the thigh component of the prosthesis or as the thigh socket, serves to receive the stump (not shown). Arranged on the prosthesis socket 1, there is a prosthetic knee joint 2 which, in the present case, is designed as a monocentric knee joint, and a below-knee component 3 is mounted so as to pivot about a pivot axis, relative to the thigh socket 1. A prosthetic foot 4 is arranged at the distal end of the below-knee component 3. The prosthetic device is shown in a terminal stance phase, the prosthetic foot 4 still located on the ground. Arranged inside the below-knee component 3 there is a resistance device 5, which offers resistance to bending, i.e. flexion, and the resistance device 5 likewise serves for variable adjustment of an extension resistance. The resistance within the resistance device is changed via an actuator which, for example, opens or closes valves or redirects hydraulic flows. Alternatively, it is likewise possible that the actuator changes Theological properties of the hydraulic fluid in order to change the resistance. Alternative changes to resistance are possible, for example the activation of brakes or the conversion of kinetic energy to electrical energy.

An inertial sensor 31 is arranged on the below-knee component 3 and records the absolute angle φus of the below-knee component. The inertial sensor 31 measures the absolute angle φus of the below-knee component 3 with respect to the vertical and can be configured as a 2D or 3D magnetic field sensor, a 2D or 3D acceleration sensor or as a gyroscope. The absolute angle φus increases as the inclination of the below-knee component 3 in the forward walking direction increases, i.e. during a clockwise pivoting about a distal point of contact with the ground. Moreover, an acceleration sensor 12 is arranged on the below-knee component 3 and can determine a tangential acceleration $a_T$, i.e. an acceleration tangential to the pivot radius of the below-knee component 3, and a radial acceleration $a_R$, i.e. an acceleration in the direction of the distal rotation point of the below-knee component 3, of the knee joint 2. With a corresponding sensor, e.g. a 3D acceleration sensor, it is also possible to detect the medial and lateral accelerations in addition or to detect only these accelerations.

Finally, a knee angle sensor 11 is provided via which the knee angle φk can be detected. The knee angle $\varphi_K$ is regarded as increasing positively in the flexion direction from the prolongation of the longitudinal extent of the below-knee component 3; the knee angle $\varphi_K$ is 0 when the longitudinal extent of the prosthesis socket 1 is flush with the axis of the longitudinal extent of the below-knee component 3. A hyperextension is regarded as a negative knee angle φk.

Figure 2:
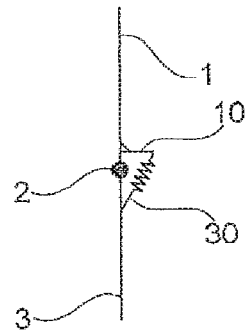
FIG. 2 shows a schematic representation of an extension stop.

The prosthetic knee joint 2 can have an elastic extension stop, which is shown schematically in FIG. 2. In addition to the schematic thigh socket 1 and the schematic below-knee component 3, which are mounted pivotably on each other about a joint axis, an abutment 10 is arranged on the upper part of the prosthetic knee joint 2. The abutment 10 is substantially rigid and, in the extended state as shown in FIG. 2, an elastic stop element 30 bears on the rigid abutment 10. A slight hyperextension is permitted by the spring design and, from knowledge of the spring rate of the stop element 30, the knee moment acting in the extension direct on can be calculated from the knee angle $\varphi_K$. Of course, it is also possible to arrange the abutment 10 on the below-knee component and to arrange the elastic stop element on the upper part 1.

To control the enablement of a swing phase, several parameters can be used, namely the forward inclination of the below-knee component 3, i.e. a positive below-knee angle $\varphi_{US}$ of the below-knee component 3, a forward rotation of the lower leg in the walking direction, i.e. an increase in the absolute angle $\varphi_{US}$ of the below-knee component 3, an acceleration of the knee joint, in order in particular to determine the state of movement of the prosthetic foot 4 at the sole level, and the knee angle $\varphi_K$ and a knee angle velocity $\omega_K$, which can be calculated from the first time derivative of the knee angle $\varphi_K$.

Figure 3:
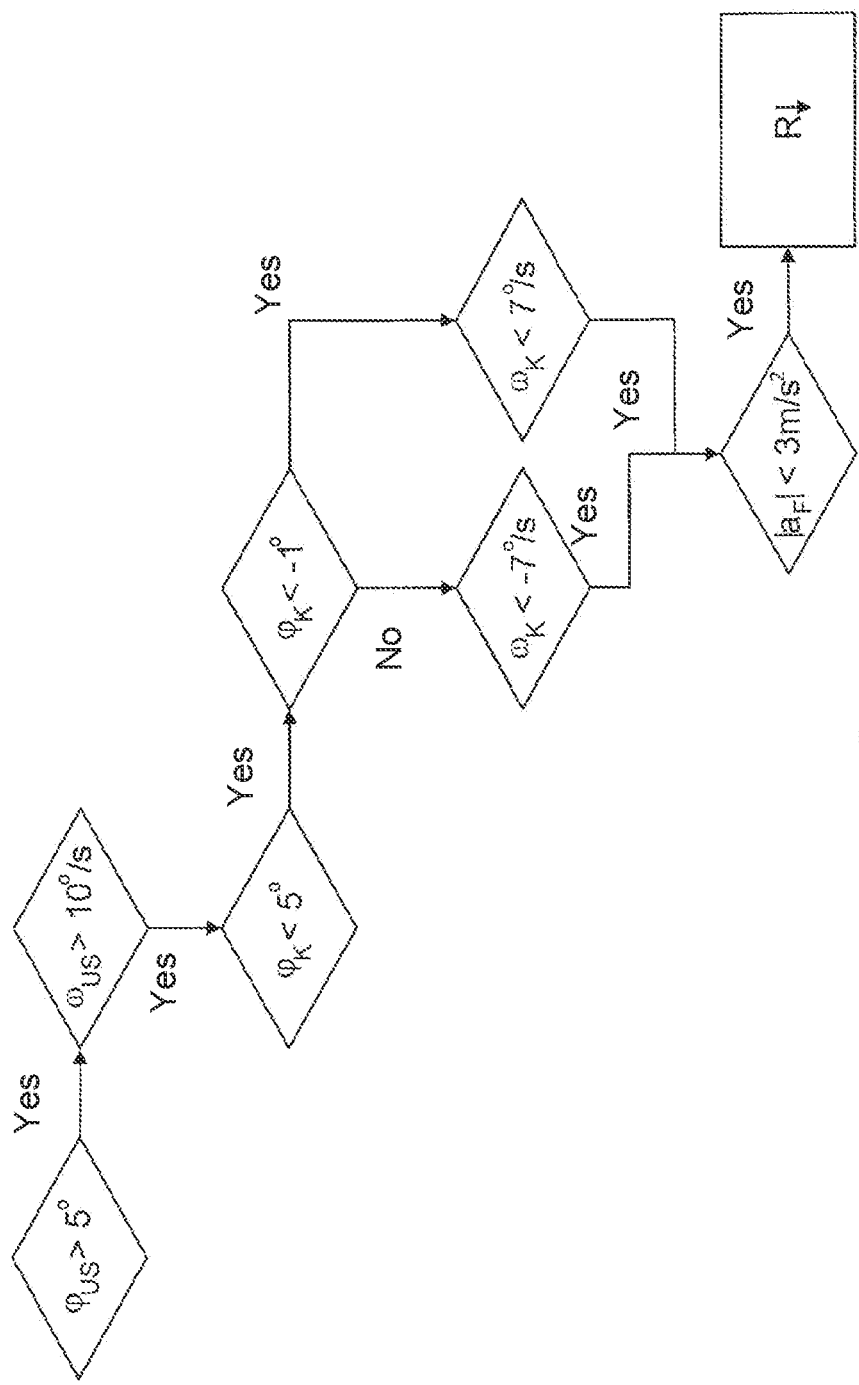
FIG. 3 shows an example of a control sequence.

FIG. 3 shows a schematic control sequence. In order to enable a swing phase and to reduce the flexion resistance R of the resistance device 5, the forward inclination is first determined, i.e. the positive absolute angle $\varphi_{US}$ of the below-knee component 3 relative to the vertical. If the absolute angle $\varphi_{US}$ is above a set limit value, for example 5°, the first condition for enablement of the swing phase is met. If, in addition, a forward rotation in the form of a lower leg angular velocity $\omega_{US}$ is detected, it can be assumed that the lower leg is in movement; a forward rotation of >10°/s, for example, can be assumed as limit value. As soon as these limit values are met or exceeded, a check is made to ascertain whether the knee angle $\varphi_K$ corresponds to a set limit value. In the terminal stance phase, which is adopted before initiation of the swing phase, the prosthetic knee joint 2 is situated in an extended or almost extended position, and a hyperextension can even occur in the case of an elastic extension stop. If a limit value for the knee angle $\varphi_K$, which is <5° and can also assume negative values, is not reached, then a further condition for initiating the enablement of a swing phase is met. The knee moment acting in the extension direction can be calculated using the knee angle $\varphi_K$ and the known data of the spring device in the elastic extension stop.

In the case of a negative knee angle $\varphi_K$ i.e. in the case of hyperextension, a check is made to ascertain how great the knee angle velocity $\omega_K$ is. If the latter is below a limit value, for example below 7°/s, it can be assumed that there is no or only slight knee flexion and knee dynamic, which is likewise characteristic for a terminal stance phase. If there is no hyperextension, a check is made to ascertain whether the negative angular velocity is below a limit value, and the question here is how great is the knee angle velocity in the flexion direction or extension direction. If the determined knee angle velocities $\omega_K$ are below the required limit values, the extent of the acceleration $a_F$ at sole level is calculated, which is based on the relative position of the acceleration vector with respect to the prosthetic foot 4. If the acceleration $a_F$ at sole level is below a limit value, for example below 3 m/s$^2$, it is to be assumed that the kinematic contact conditions between the prosthetic foot 4 and the ground correspond to those of a terminal stance phase and, consequently, the reduction of the resistance R of the resistance device 5 can be initiated.

For the clear decision between forward heel-toe walking via the prosthetic foot 4, i.e. a forward stride, and a rearward swing-through of the prosthesis under the body, for example in the swing phase of a rearward step, all the steps and questions are necessary that follow the establishment of a forward inclination and forward rotation of the below-knee component 3. For this purpose, a hyperextension of the prosthetic knee joint 2 counter to an elastic extension stop 10, 30 or a strongly extending movement at a low knee angle $\varphi_K$ is needed, which can be measured by the knee angle sensor 11. In addition, the acceleration sensor 12 determines whether the extension moment about the knee joint is applied statically or dynamically. In particular, the linear accelerations of the prosthesis at the sole level are calculated. Assuming that the forward inclination, i.e. the positive absolute angle (pus, and a forward rotation of the below-knee component are given, case distinctions can be made on the basis of accelerations and knee moments and, on the basis of these case distinctions, the flexion resistance R is either maintained at a high stance-phase flexion level or is reduced to a swing-phase level.

If there is an insufficient extension moment or a sufficient flexion moment about the prosthetic knee joint 2, or if the knee angle velocity $\omega_K$ is either extending or the prosthetic knee joint 2 is in hyperextension, there can be no enablement of the swing phase.

If the prosthetic knee joint experiences an extension moment about the knee axis on account of dynamic forces, for example on account of the inertial forces of the prosthetic foot 4 and of the below-knee component 3, a hyperextension in the knee joint or a stretching movement can be measured. If the below-knee component 3 thus moves, this situation corresponds to that of a pendulum, such that there is no enablement of a swing phase.

Enablement of a swing phase accordingly takes place when an extension moment about the knee axis is caused by static forces, such as ground reaction force, and stump forces acting on the prosthetic knee joint. In this case, a hyperextension or a greatly stretching movement of the knee joint is measured, but no or only slight acceleration $a_F$ at sole level. Such a situation is characteristic of the terminal stance phase, in which the prosthesis, loaded in the walking direction, rolls heel to toe over the foot. In this situation, the resistance R is reduced.

The characteristic of the elastic hyperextension, in particular the spring characteristic of the elastic extension stop, and the threshold values for the knee angle $\varphi_K$, the knee angle velocity $\omega_K$ and the admissible accelerations $a_F$ for enablement of a swing phase have to be chosen such that, on the one hand, a clear distinction can be made as to whether a swing phase is enabled and, on the other hand, also a slight hyperextension is achieved, for example by users with low body weight and with small steps and slow walking speeds.

If, for example, within the first 5° of a knee flexion movement after enablement of the resistance device 5 to a reduced flexion resistance R, an acceleration $a_F$ of a magnitude above a defined threshold is established, for example by striking against an obstacle, it is possible for the flexion resistance R to be immediately switched back to a high level of stance-phase flexion damping, in order to avoid unwanted flexion in an emergency.

All of the measured signals of the sensors can be filtered in order to be able to compensate for measurement inaccuracies. For the acceleration conditions, asymmetrical limit values can be set in order to be able to perform individual adaptation to the respective gait situation and movement directions.

The proposed control arrangement does not require direct measurement of forces, and it is therefore possible to do without force sensors that can in some cases be sensitive and difficult to evaluate. The sensors used are exclusively knee angle sensors, inertial angle sensors such as gyroscopes, and acceleration sensors. The moments about the knee axis, particularly in the extension direction, can be easily determined with these sensors, since the parameters of an elastic extension stop are detected and used as a basis for the calculation.

The easily determinable linear and angular accelerations are used to calculate the state of movement of the prosthesis, in particular to identify the state of movement of the prosthetic foot 4. Through the logical linkage of forces and moments with accelerations, it is possible to distinguish between static forces and dynamic forces and moments, such that this distinction permits detection of the walking pattern. In this way, a distinction can easily be made as to whether a free swing-through or a terminal stance phase is present.

The control according to the method described moreover also permits the reliable enablement of the swing phase even with slow walking speeds, small strides and on soft ground, for example loose sand or snow. The control is independent of the patient's weight and is able to ensure the patient can safely walk backward.

Figure 4:
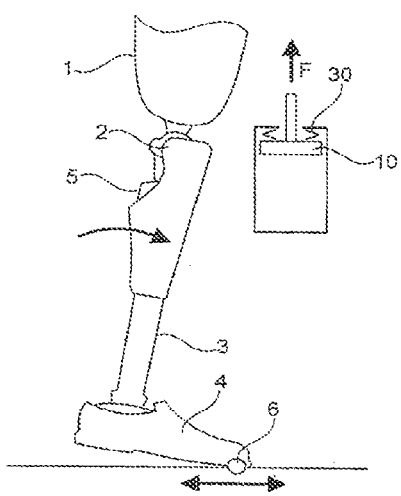
FIG. 4 shows a schematic representation of a control concept.
Figure 4:
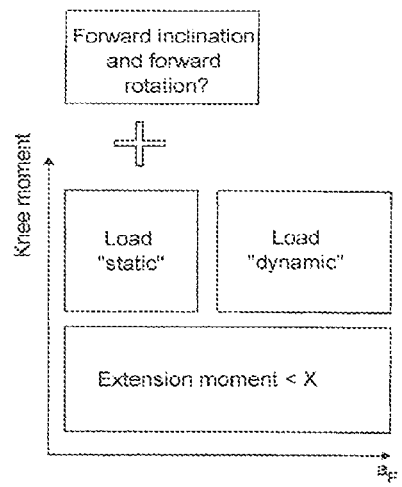

FIG. 4 shows a schematic view of a control concept of a prosthetic knee joint, the set-up of the prosthesis corresponding to that of FIG. 1. It is also possible in principle to use the control concept in orthoses, particularly in what is called a KAFO (knee ankle foot orthosis). The prosthesis socket 1 or the thigh component is connected to the below-knee component 3 via the prosthetic knee joint 2. The prosthetic foot 4 arranged at the distal end of the below-knee component 3. The resistance device 5 is likewise situated inside the below-knee component 3. The elastic extension stop, which can be arranged in particular inside the resistance device 5, is shown on the right next to the schematic representation of the prosthetic device. The prosthetic device is located in the extended stride position in the terminal stance phase, which means that, in the front area of the foot, a resting and rotating point 6 is created about which the prosthetic device rotates. On account of the lever between the longitudinal axis of the below-knee component 3 and the resting point 6, an extension moment is applied around the knee joint 2, and this has the effect that the abutment 10, which in this case is movable and part of a hydraulic piston, is pressed against the stop element 30 in the form of a spring. At the same time, it is ascertained whether the prosthetic device has a forward inclination, which is indicated by the curved arrow. If an absolute angle $\varphi_{US}$ is present, i.e. an inclination to the vertical in the clockwise direction in the illustrative embodiment shown, and if a forward rotation takes place, i.e. an increase of the absolute angle $\varphi_{US}$ in the forward direction of walking, wherein the rotation takes place about the distal resting point 6, further criteria are given for determining the instantaneous state and the phase within a gait cycle or a gait sequence. The extension moment can be calculated from the spring rate of the stop element 30 and the knee angle, in this case the negative knee angle $\varphi_K$.

To rule out the possibility of the below-knee component simply swinging freely about the knee joint 2, the linear acceleration $a_F$ at the contact point 6 is determined. If this acceleration is 0 or very low, it can be assumed that the prosthetic foot 4 and the resting point 6 have ground contact, such that a stationary rotation point is present at the resting point 6. The load is virtually static. In the case of a static load, a forward inclination and forward rotation and, if appropriate, hyperextension, if the extension moment does not exceed a limit value X, the flexion resistance R of the resistance device 5 is then reduced, such that a bending of the prosthetic knee joint 2 can easily take place.

The invention claimed is:

1. A method for controlling an artificial orthotic or prosthetic knee joint, the orthotic or prosthetic knee joint including a resistance device, at least one sensor, and a below-knee component, the method comprising:
   determining sensor data via the at least one sensor during use of the orthotic or prosthetic knee joint;
   determining at least one of a linear acceleration of the below-knee component, an extended stride position of a prosthesis or orthosis having the artificial prosthetic or orthotic knee joint, a knee angle, a knee angle velocity, and/or an angular velocity of the below-knee component with the sensor data;
   comparing at least one of the determined linear acceleration, the determined extended stride position, the determined knee angle, the determined knee angle velocity, and/or the determined angular velocity with at least one threshold value therefor;
   reducing a flexion resistance if the threshold value is reached;
   determining an absolute angle of the below-knee component in order to detect a terminal stance phase;
   determining a knee moment about an axis of the orthotic or prosthetic knee joint in order to detect the terminal stance phase; and
   reducing the flexion resistance if a predefined limit value for the absolute angle of the below-knee component is exceeded such that the below-knee component has a forward inclination and if the knee moment is acting in an extension direction, wherein determining at least one of a linear acceleration of the below-knee component, an extended stride position of a prosthesis or orthosis having the artificial prosthetic or orthotic knee joint, a knee angle, a knee angle velocity, and an angular velocity of the below-knee component with the sensor data comprises determining the linear acceleration of the below-knee component, and reducing the flexion resistance when the extended stride position is present, and wherein the threshold value is zero acceleration in a horizontal direction.

2. The method as claimed in claim 1, wherein determining at least one of a linear acceleration of the below-knee component, an extended stride position of a prosthesis or orthosis having the artificial prosthetic or orthotic knee joint, a knee angle, a knee angle velocity, and an angular velocity of the below-knee component with the sensor data comprises determining the extended stride position of a prosthesis or orthosis having the artificial prosthetic or orthotic knee joint, and reducing the flexion resistance when the extended stride position is present.

3. The method as claimed in claim 1, further comprising measuring the absolute angle of the below-knee component from an absolute angle of a thigh component and a knee angle or directly with an inertial angle sensor.

4. The method as claimed in claim 1, wherein determining at least one of a linear acceleration of the below-knee component, an extended stride position of a prosthesis or orthosis having the artificial prosthetic or orthotic knee joint, a knee angle, a knee angle velocity, and an angular velocity of the below-knee component with the sensor data comprises determining the knee angle via the at least one sensor, and reducing the flexion resistance if a predefined limit value for the knee angle is not reached.

5. The method as claimed in claim 1, wherein determining at least one of a linear acceleration of the below-knee component, an extended stride position of a prosthesis or orthosis having the artificial prosthetic or orthotic knee joint, a knee angle, a knee angle velocity, and an angular velocity of the below-knee component with the sensor data comprises determining the knee angle velocity, and reducing the flexion resistance only when a limit value is exceeded.

6. The method as claimed in claim 1, wherein determining at least one of a linear acceleration of the below-knee component, an extended stride position of a prosthesis or orthosis having the artificial prosthetic or orthotic knee joint, a knee angle, a knee angle velocity, and an angular velocity of the below-knee component with the sensor data comprises calculating or detecting the angular velocity of the below-knee component via the at least one sensor, and reducing the flexion resistance only when the angular velocity is below a limit value.

7. The method as claimed in claim 1, wherein, after a reduction of the flexion resistance, the method further comprising increasing the flexion resistance again if, within a predefined time interval, no bending of the knee joint took place, or if, within an enclosed knee angle, a limit value for an acceleration is exceeded.

8. The method as claimed in claim 1, wherein the at least one sensor includes an inertial sensor and an acceleration sensor.

9. A method to control an artificial orthotic or prosthetic knee joint, the method comprising:
   providing an inertial measurement system, a below-knee component positioned on the orthotic or prosthetic knee joint, and a resistance device, the below-knee component including a sole member;
   determining sensor data via the inertial measurement system during use of the orthotic or prosthetic knee joint;
   determining a linear acceleration at a level of the sole member, an extended stride position of a prosthesis or orthosis having the artificial prosthetic or orthotic knee joint, a knee angle, a knee angle velocity, and an angular velocity of the below-knee component with the sensor data;

comparing at least one of the determined linear acceleration, the determined extended stride position, the determined knee angle, the determined knee angle velocity, and the determined angular velocity with at least one threshold value;

reducing a flexion resistance if the threshold value is reached;

determining an absolute angle of the below-knee component in order to detect a terminal stance phase; and reducing the flexion resistance if a predefined limit value for the absolute angle of the below-knee component is exceeded such that the below-knee component has a forward inclination and if the linear acceleration is zero in a horizontal direction.

10. The method as claimed in claim 9, wherein determining at least one of a linear acceleration of the below-knee component, an extended stride position of a prosthesis or orthosis having the artificial prosthetic or orthotic knee joint, a knee angle, a knee angle velocity, and an angular velocity of the below-knee component with the sensor data comprises determining the extended stride position of a prosthesis or orthosis having the artificial prosthetic or orthotic knee joint, and reducing the flexion resistance when the extended stride position is present.

11. The method as claimed in claim 9, wherein determining at least one of a linear acceleration of the below-knee component, an extended stride position of a prosthesis or orthosis having the artificial prosthetic or orthotic knee joint, a knee angle, a knee angle velocity, and an angular velocity of the below-knee component with the sensor data comprises determining the linear acceleration of the below-knee component, and reducing the flexion resistance when the extended stride position is present, and wherein the threshold value is zero acceleration in a horizontal direction.

12. The method as claimed in claim 11, further comprising measuring the absolute angle of the below-knee component from an absolute angle of a thigh component and a knee angle or directly with an inertial angle sensor.

13. The method as claimed in claim 9, wherein determining at least one of a linear acceleration of the below-knee component, an extended stride position of a prosthesis or orthosis having the artificial prosthetic or orthotic knee joint, a knee angle, a knee angle velocity, and an angular velocity of the below-knee component with the sensor data comprises determining the knee angle via the at least one sensor, and reducing the flexion resistance if a predefined limit value for the knee angle is not reached.

14. The method as claimed in claim 9, wherein determining at least one of a linear acceleration of the below-knee component, an extended stride position of a prosthesis or orthosis having the artificial prosthetic or orthotic knee joint, a knee angle, a knee angle velocity, and an angular velocity of the below-knee component with the sensor data comprises determining the knee angle velocity, and reducing the flexion resistance only when a limit value is exceeded.

15. The method as claimed in claim 9, wherein determining at least one of a linear acceleration of the below-knee component, an extended stride position of a prosthesis or orthosis having the artificial prosthetic or orthotic knee joint, a knee angle, a knee angle velocity, and an angular velocity of the below-knee component with the sensor data comprises calculating or detecting the angular velocity of the below-knee component via the at least one sensor, and reducing the flexion resistance only when the angular velocity is below a limit value.

16. The method as claimed in claim 9, wherein, after a reduction of the flexion resistance, the method further comprising increasing the flexion resistance again if, within a predefined time interval, no bending of the knee joint took place, or if, within an enclosed knee angle, a limit value for an acceleration is exceeded.

17. The method as claimed in claim 9, wherein the threshold value is zero acceleration in a horizontal direction.

18. The method as claimed in claim 9, wherein the inertial measurement system includes an inertial sensor and an acceleration sensor.

19. A method to control an artificial orthotic or prosthetic knee joint, the method comprising:

providing at least one sensor, a below-knee component positioned on the orthotic or prosthetic knee joint, and a resistance device, the below-knee component including a sole member, the at least one sensor including an inertial sensor and an acceleration sensor;

determining sensor data via the at least one sensor during use of the orthotic or prosthetic knee joint;

changing a flexion resistance applied by the resistance device using the sensor data;

determining a linear acceleration at a level of the sole member with the sensor data;

reducing the flexion resistance if the linear acceleration is zero in a horizontal direction;

determining an absolute angle of the below-knee component in order to detect a terminal stance phase; and reducing the flexion resistance if a predefined limit value for the absolute angle of the below-knee component is exceeded such that the below-knee component has a forward inclination.

* * * * *